United States Patent
Skaggs (10) Patent No.: US 9,220,536 B2
(45) Date of Patent: Dec. 29, 2015

(54) SYSTEM AND METHOD FOR CORRECTION OF A SPINAL DISORDER

(71) Applicant: Warsaw Orthopedic, Inc, Warsaw, IN (US)

(72) Inventor: David Skaggs, Los Angeles, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/051,512

(22) Filed: Oct. 11, 2013

(65) Prior Publication Data

US 2014/0039559 A1  Feb. 6, 2014

Related U.S. Application Data

(63) Continuation of application No. 13/343,564, filed on Jan. 4, 2012, now Pat. No. 8,617,220.

(51) Int. Cl.
*A61F 2/44* (2006.01)
*A61B 17/70* (2006.01)
*A61B 17/86* (2006.01)
*A61B 17/00* (2006.01)

(52) U.S. Cl.
CPC ............. *A61B 17/7002* (2013.01); *A61B 17/70* (2013.01); *A61B 17/7022* (2013.01); *A61B 17/7031* (2013.01); *A61B 17/7044* (2013.01); *A61B 17/8695* (2013.01); *A61B 2017/00004* (2013.01)

(58) Field of Classification Search
CPC ............... A61B 17/70; A61B 17/7053; A61B 17/7047; A61B 17/7067; A61B 17/707; A61B 17/7083; A61B 17/7071
USPC ................................ 606/246–279; 623/17.11
See application file for complete search history.

(56) References Cited

U.S. PATENT DOCUMENTS

| | | | |
|---|---|---|---|
| 4,269,178 A * | 5/1981 | Keene | 606/276 |
| 5,620,444 A * | 4/1997 | Assaker | 606/276 |
| 6,299,613 B1 | 10/2001 | Ogilvie et al. | |
| 2002/0120270 A1* | 8/2002 | Trieu et al. | 606/61 |
| 2005/0277919 A1* | 12/2005 | Slivka et al. | 606/61 |
| 2007/0073293 A1 | 3/2007 | Martz et al. | |
| 2007/0276384 A1* | 11/2007 | Spratt | 606/72 |
| 2007/0288014 A1* | 12/2007 | Shadduck et al. | 606/61 |
| 2008/0319487 A1* | 12/2008 | Fielding et al. | 606/263 |
| 2009/0099605 A1* | 4/2009 | Fallin et al. | 606/252 |
| 2010/0152779 A1* | 6/2010 | Allard et al. | 606/279 |

* cited by examiner

*Primary Examiner* — Mary Hoffman
*Assistant Examiner* — Tara R Carter (57) ABSTRACT

A surgical system and method for fusionless correction of a spine disorder are provided. The method comprising the steps of: providing access to a spine; providing a longitudinal element extending between a first end including a first fixation element and a second end including a second fixation element; engaging the first fixation element with a first costovertebral surface and engaging the second fixation element with a second costovertebral surface such that the longitudinal element is disposed in a costotransverse orientation along a selected section of the spine; and preventing growth of the selected section of the spine with the longitudinal element.

19 Claims, 12 Drawing Sheets

SYSTEM AND METHOD FOR CORRECTION OF A SPINAL DISORDER

This application is a continuation of U.S. patent application Ser. No. 13/343,564, filed on Jan. 4, 2012, which is expressly incorporated herein by reference, in its entirety.

TECHNICAL FIELD

The present disclosure generally relates to medical devices for the treatment of musculoskeletal disorders, and more particularly to a surgical system and method for fusionless correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods, for stabilization of a treated section of a spine. This disclosure describes an improvement over these prior art technologies.

SUMMARY

Accordingly, a surgical system and method for fusionless correction of a spine disorder is provided. In one embodiment, in accordance with the principles of the present disclosure, a method for fusionless correction of a spine disorder is provided. The method comprising the steps of: providing access to a spine; providing a longitudinal element extending between a first end including a first fixation element and a second end including a second fixation element; engaging the first fixation element with a first costovertebral surface and engaging the second fixation element with a second costovertebral surface such that the longitudinal element is disposed in a costotransverse orientation along a selected section of the spine; and preventing growth of the selected section of the spine with the longitudinal element.

In one embodiment, the method comprises the steps of: providing access to a surgical site adjacent a selected section of a spine along a substantially posterior approach; providing a tether extending between a first end comprising a first fastener configured to penetrate bone and a second end including a second fastener configured to penetrate bone; threading the tether in a costotransverse orientation along a plurality of vertebral levels of the spine; engaging the first fastener to penetrate a first costovertebral surface and engaging the second fastener to penetrate a second costovertebral surface such that the tether is disposed along the selected section of the spine; and preventing growth of the selected section of the spine with the tether.

In one embodiment, the method comprises the steps of: providing access to a surgical site adjacent a selected section of a spine along a substantially posterior approach; providing a tether extending between a first end comprising a first washer configured for non-penetrating engagement and a second end including a second washer configured for non-penetrating engagement; threading the tether in a costotransverse orientation along a plurality of vertebral levels of the spine; engaging the first washer with a first costovertebral surface and engaging the second washer with a second costovertebral surface such that the tether is disposed along the selected section of the spine; and preventing growth of the selected section of the spine with the tether.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the surgical system and related methods of use disclosed are discussed in terms of medical devices for the treatment of musculoskeletal disorders and more particularly, in terms of a surgical system and method for fusionless correction of a spine disorder. It is envisioned that the surgical system and method may be employed in applications such as fusionless correction of deformities, such as scoliosis. For example, the surgical system and method can include attachment of a tether to a convex side of a spine that is curved due to scoliosis. It is contemplated that while the tether may be affixed to a first side of each of a plurality of vertebrae to prevent growth of vertebrae of the first side, the system allows for growth and adjustments to a second side of the plurality of vertebrae.

In one embodiment, the system and method include placing a tether in a costovertebral space adjacent a posterior side of a patient. It is envisioned that the tether can be placed on an anterior side of a transverse process. In one embodiment, the tether is engaged and/or fastened to vertebrae using screws and/or fasteners. In one embodiment, the tether is engaged and/or fastened to vertebrae using a fixation element, such as, for example, a washer, at a transverse process/rib junction adjacent a costovertebral space. It is contemplated that the tether may be fixed with vertebrae in two or more locations along a length of the tether.

It is envisioned that the system and method provide features along a sagittal plane of a patient whereby the tether is positioned anterior to a pedicle to reduce undesired lordosis. It is further envisioned that the system and method provide features along a coronal plane of a patient whereby the tether is positioned in a lateral orientation relative to a pedicle to provide more correction in the coronal plane.

In one embodiment, the components of the system are provided along a surgical pathway along a posterior approach such that the tether is disposed in the space between a transverse process and a rib head. This configuration can avoid undesired engagement with body structures, such as, for example, a spinal canal and vascular structures, in that the surgical pathway is created via muscle-splitting through relatively bloodless planes. For example, the costovertebral space can include a costotransverse ligament, which can be easily penetrated bluntly. In one embodiment, the system includes an anchor that supports a tensile load over a transverse process and a rib head. It is contemplated that one or all of the components of the surgical system may be disposable, peel-pack, pre-packed sterile devices. One or all of the components of the surgical system may be reusable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-9, there is illustrated components of a surgical system, such as, for example, a fusionless correction system in accordance with the principles of the present disclosure.

The components of the correction system can be fabricated from biologically acceptable materials suitable for medical applications, including metals, synthetic polymers, ceramics, bone material, tissue and/or their composites, depending on the particular application and/or preference of a medical practitioner. For example, the components of the correction system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the system may have material composites, including the above materials, to achieve various desired characteristics such as strength, rigidity, elasticity, compliance, biomechanical performance, durability and radiolucency or imaging preference. The components of the system, individually or collectively, may also be fabricated from a heterogeneous material such as a combination of two or more of the above-described materials. The components of the system may be monolithically formed, integrally connected or include fastening elements and/or instruments, as described herein.

The system is employed, for example, with an open, mini-open or minimally invasive surgical technique to attach a longitudinal element to a first side, such as, for example, a convex side of a spine that has a spinal disorder. In one embodiment, the longitudinal element may be affixed to the convex side of each of a plurality of vertebrae such that the system prevents growth of vertebrae of a selected section of the spine while allowing for growth and adjustments to a second side, such as, for example, a concave side of the plurality of vertebrae for a correction treatment to treat various spine pathologies, such as, for example, adolescent idiopathic scoliosis and Scheuermann's kyphosis.

Figure 1:
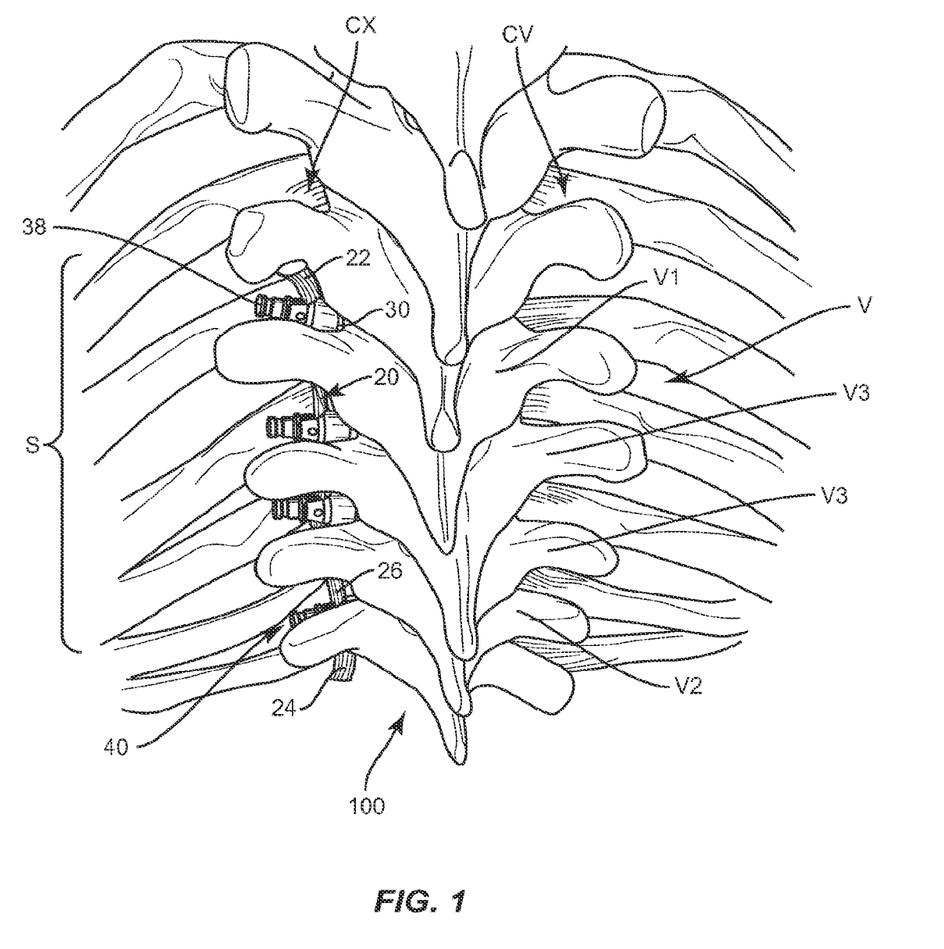
FIG. 1 is a perspective view of one particular embodiment of a system disposed with vertebrae in accordance with the principles of the present disclosure.
Figure 2:
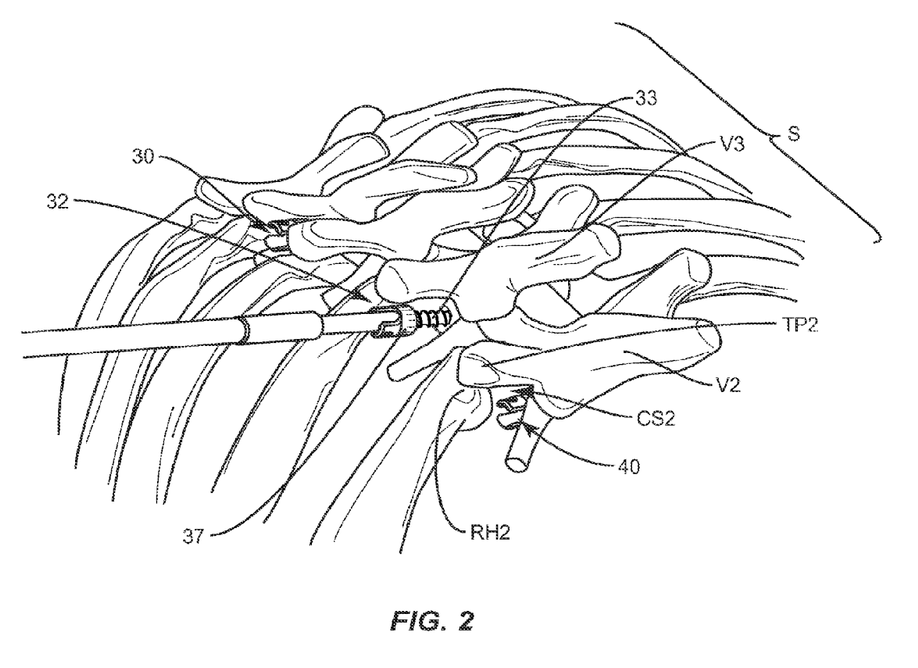
FIG. 2 is a perspective view of components of the system shown in FIG. 1 engaging vertebrae.
Figure 3:
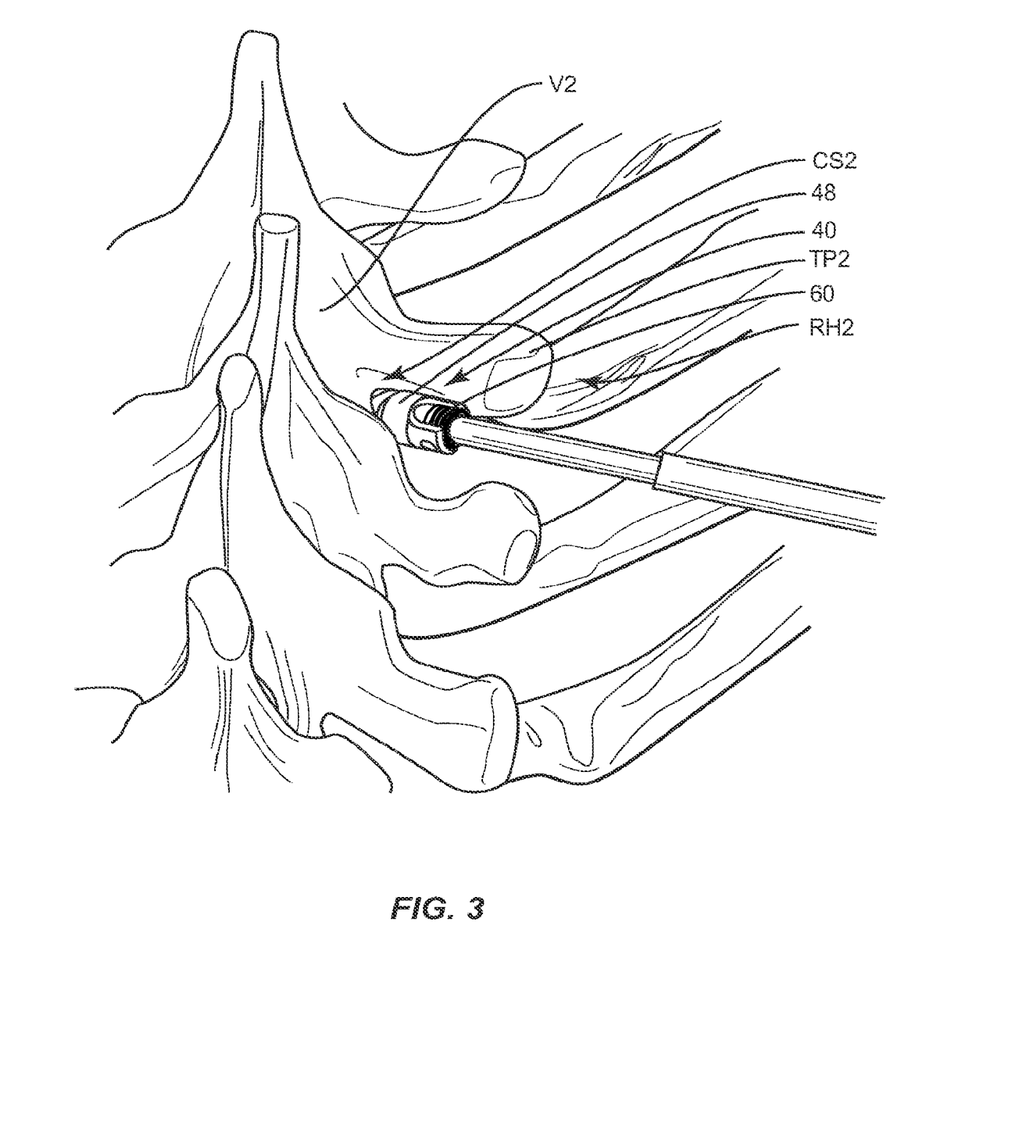
FIG. 3 is a perspective view of the components and vertebrae shown in FIG. 2.

The present system includes a longitudinal element, such as, for example, a tether 20 that extends between a first end 22 and a second end 24. Tether 20 has a flexible configuration, which includes movement in a lateral or side to side direction and prevents expanding and/or extension in an axial direction upon fixation with vertebrae, as will be described. It is envisioned that all or only a portion of tether 20 may have a semi-rigid, rigid or elastic configuration, and/or have elastic properties such that tether 20 provides a selective amount of expansion and/or extension in an axial direction. It is further envisioned that tether 20 may be compressible in an axial direction. Tether 20 can include a plurality of separately attachable or connectable portions or sections, such as bands or loops, or may be monolithically formed as a single continuous element.

Tether 20 has an outer surface 26 and a uniform thickness/diameter. It is envisioned that outer surface 26 may have various surface configurations, such as, for example, rough, threaded for connection with surgical instruments, arcuate, undulating, porous, semi-porous, dimpled, polished and/or textured according to the requirements of a particular application. It is contemplated that the thickness defined by tether 20 may be uniformly increasing or decreasing, or have alternate diameter dimensions along its length. It is further contemplated that tether 20 may have various cross section configurations, such as, for example, oval, oblong, triangular, rectangular, square, polygonal, irregular, uniform, non-uniform, variable and/or tapered.

It is contemplated that tether 20 may have various lengths, according to the requirements of a particular application. It is further contemplated that tether 20 may be braided, such as a rope, or include a plurality elongated elements to provide a predetermined force resistance. It is envisioned that tether 20 may be made from autograft and/or allograft, as described above, and be configured for resorbable or degradable applications.

It is contemplated that the longitudinal element may include one or a plurality of flexible wires, staples, cables, ribbons, artificial and/or synthetic strands, rods, plates, springs, and combinations thereof. In one embodiment, the longitudinal element is a cadaver tendon. In one embodiment, the longitudinal element is a solid core. In one embodiment, the longitudinal element is tubular.

The system includes a first fixation element, such as, for example, a bone screw 30 connected with first end 22 and a second fixation element, such as, for example, a bone screw 40 connected with second end 24. Screws 30, 40 may be monolithically formed, integrally connected or attached with fastening elements to tether 20. The system includes a plurality of third fixation elements, such as, for example, bone screws 32 disposed intermediate first end 22 and second end 24, and connected to tether 20 between screws 30, 40 along the length of tether 20. Screws 32 may be monolithically formed, integrally connected or attached with fastening elements to tether 20. It is envisioned that one or a plurality of screws 32 may be connected with tether 20. It is further envisioned that the system may not include screw(s) 32.

Screws 30, 40, 32 are configured for penetrating fixation with tissue of vertebrae along a plurality of vertebral levels. Each of screws 30, 40, 32 are disposed to engage a separate vertebral level. It is contemplated one or a plurality of fixation elements may be employed with a single vertebral level. It is further contemplated that the fixation elements may be engaged with vertebrae in various orientations, such as, for example, series, parallel, offset, staggered and/or alternate vertebral levels. It is envisioned that the fixation elements may include one or a plurality of anchors, tissue penetrating screws, conventional screws, expanding screws, wedges, anchors, buttons, clips, snaps, friction fittings, compressive fittings, expanding rivets, staples, nails, adhesives, posts, fixation plates and/or posts. These fixation elements may be coated with an osteoinductive or osteoconductive material to enhance fixation, and/or include one or a plurality of therapeutic agents.

In assembly, operation and use, a fusionless correction system, similar to the system described above, is employed with a surgical procedure, such as, for a correction treatment to treat adolescent idiopathic scoliosis and/or Scheuermann's kyphosis of a spine. It is contemplated that one or all of the components of the fusionless correction system can be delivered or implanted as a pre-assembled device or can be assembled in situ. The fusionless correction system may be completely or partially revised, removed or replaced.

For example, as shown in FIGS. 1-9, the fusionless correction system can be employed with a surgical correction treatment of an applicable condition or injury of an affected section of a spinal column and adjacent areas within a body, such as, for example, a first vertebra V1, a second vertebra V2 and a plurality of vertebra disposed therebetween, such as, for example, third vertebrae V3, of vertebrae V.

In use, to treat a selected section S of vertebrae V, a medical practitioner obtains access to a surgical site including vertebrae V in any appropriate manner, such as through incision and retraction of tissues. It is envisioned that the fusionless correction system can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder. The configuration and dimension of tether 20 is determined according to the configuration and dimension of selected section S and the requirements of a particular application.

Figure 4:
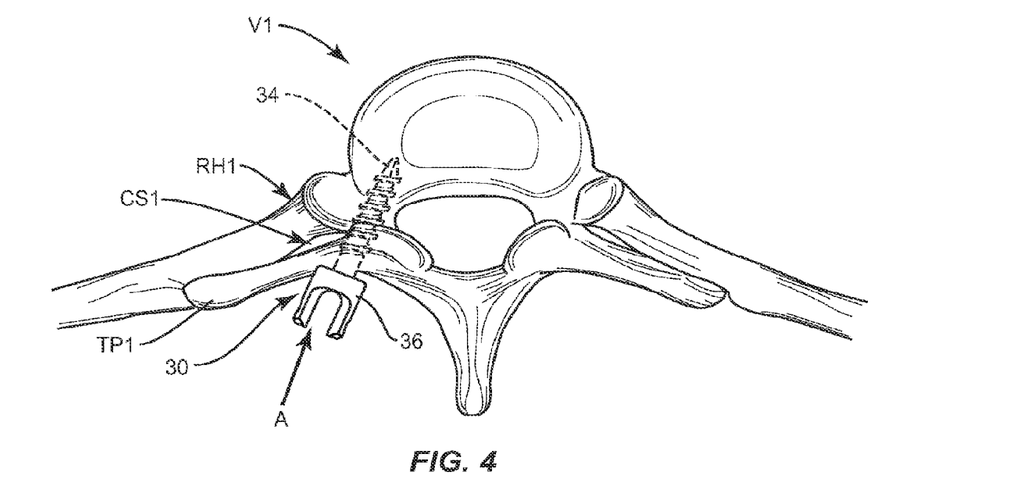
FIG. 4 is a plan view, in cross section, of the components and vertebrae shown in FIG. 2.
Figure 5:
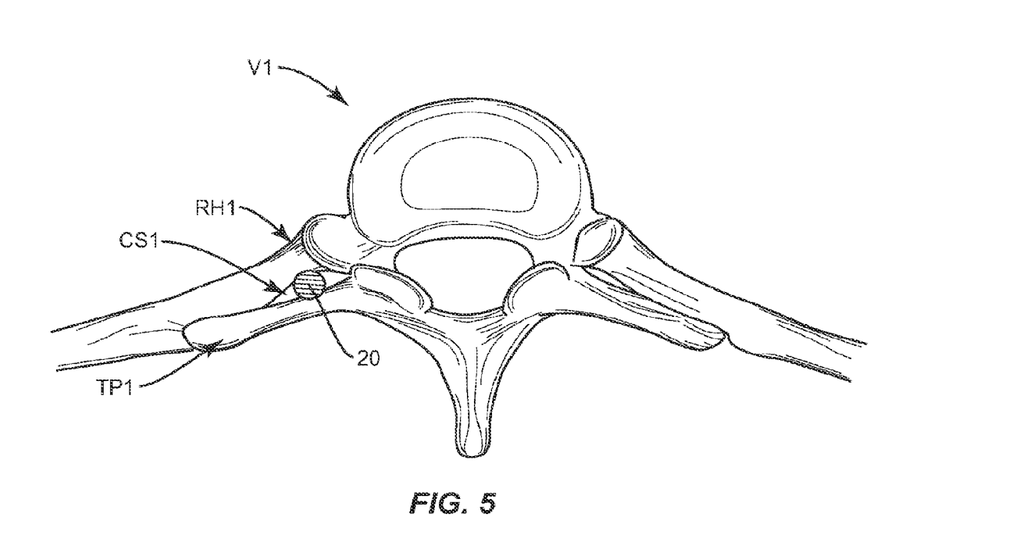
FIG. 5 is a plan view, in cross section, of the components and vertebrae shown in FIG. 1.
Figure 6:
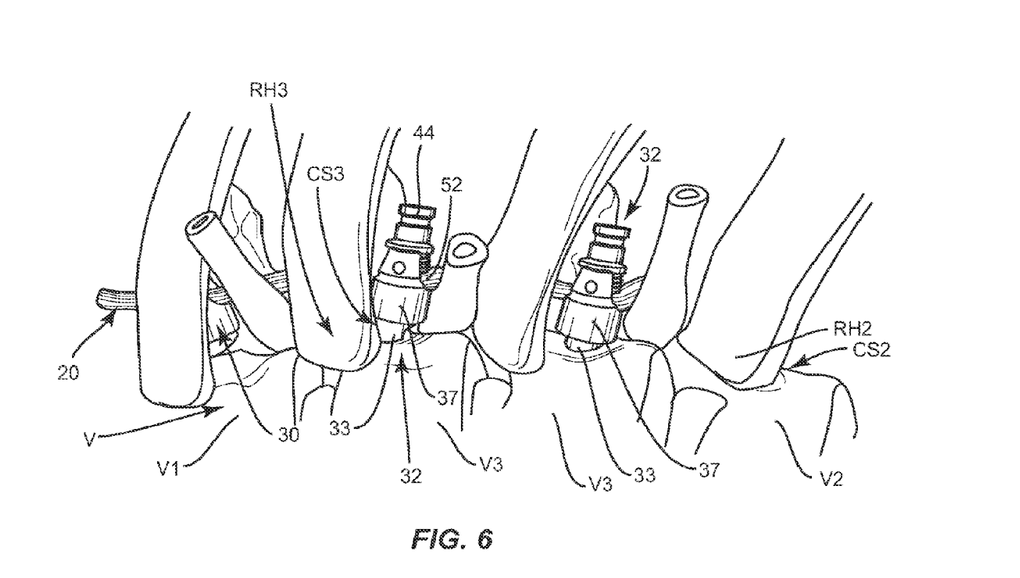
FIG. 6 is a break away perspective view of the components and vertebrae shown in FIG. 1.
Figure 7:
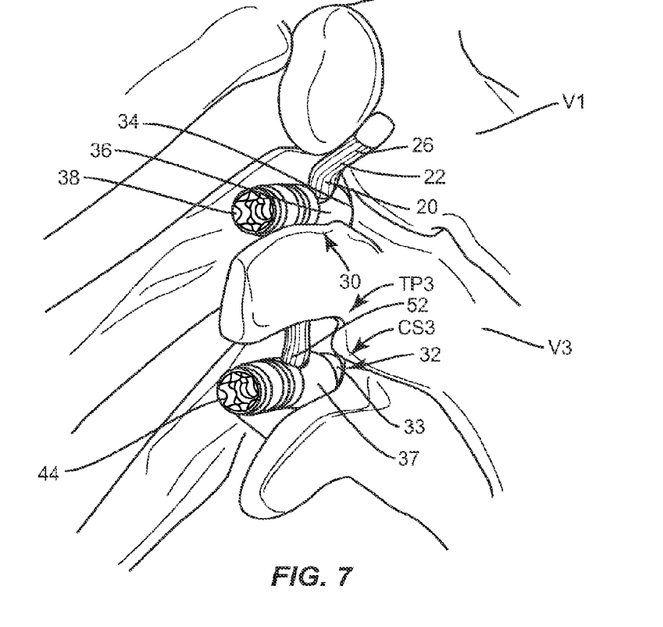
FIG. 7 is a break away perspective view of the components and vertebrae shown in FIG. 1.

An incision is made in the body of a patient and a cutting instrument (not shown) creates a surgical pathway along a substantially posterior approach, as shown by arrow A in FIG. 4, for implantation of components of the fusionless correction system within the patient body. A sleeve or cannula is used to access a costovertebral space CS1, as shown in FIG. 5, adjacent vertebra V1 and facilitate delivery and access for components of the fusionless correction system along the surgical pathway, for example, such that tether 20 is disposed in a costovertebral space CS1 between costovertebral surfaces, which include surfaces of a transverse process TP1, a rib head RH1 and vertebra V1. It is contemplated that this method and configuration avoid undesired engagement with body structures, such as, for example, a spinal canal and vascular structures, in that the surgical pathway is created via muscle-splitting through relatively bloodless planes. A preparation instrument (not shown) can be employed to prepare tissue surfaces of vertebrae V and adjacent rib surfaces, as well as for aspiration and irrigation of the region according to the requirements of a particular surgical application.

Screw 30 is configured to support a tensile load with tether 20 over costovertebral surfaces, which include surfaces of transverse process TP1 and rib head RH1. A pilot hole is made in vertebra V1 for receiving screw 30. Screw 30 is delivered along the surgical pathway adjacent costovertebral space CS1 for penetrating engagement with vertebra V1. Screw 30 includes a threaded bone engaging portion 34 that is inserted or otherwise engaged with vertebra V1, according to the particular requirements of the surgical treatment. Screw 30 has a head 36 with a bore, or through opening and a set screw 38, which is torqued on to tether 20, as will be described.

One or a plurality of screws 32 are configured to support a tensile load with tether 20 over one or a plurality of costovertebral surfaces, which include surfaces of transverse processes TP3, rib heads RH3 and vertebra V3. A pilot hole is made in vertebra V3 for receiving screw 32. Screw 32 is delivered along the surgical pathway, or an alternate surgical pathway along a substantially posterior approach, adjacent a costovertebral space CS3 for penetrating engagement with vertebra V3. Screw 32 includes a threaded bone engaging portion 33 that is inserted or otherwise engaged with vertebra V3, according to the particular requirements of the surgical treatment. Screw 32 has a head 37 with a bore, or through opening and a set screw 44, which is torqued on to tether 20.

Screw 40 is configured to support a tensile load with tether 20 over costovertebral surfaces, which include surfaces of a transverse process TP2, a rib head RH2 and vertebra V2. A pilot hole is made in vertebra V2 for receiving screw 40. Screw 40 is delivered along the surgical pathway, or an alternate surgical pathway along a substantially posterior approach, adjacent a costovertebral space CS2 for penetrating engagement with vertebra V2. Screw 40 includes a threaded bone engaging portion 46 that is inserted or otherwise engaged with vertebra V2, according to the particular requirements of the surgical treatment. Screw 40 has a head 48 with a bore, or through opening and a set screw 60, which is torqued on to tether 20.

Tether 20 is delivered along the surgical pathway to costovertebral space CS1 for attachment with screw 30. Set screw 38 of head 36 is torqued on to the portion of tether 20 disposed with screw 30 to securely fix first end 22 of tether 20 with vertebra V1. Tether 20 is disposed in costovertebral space CS1 on a posterior side of vertebra V1 such that tether 20 is disposed on an anterior side of transverse process TP1.

Tether 20 is threaded in a costotransverse orientation along vertebra V and one or a plurality of vertebra V3. Set screw 44 of head 37 is torqued on to an intermediate portion 52 of tether 20 to attach to screw 32 to securely fix intermediate portion 52 with vertebra V3. Tether 20 is disposed in costovertebral space CS3 on a posterior side of vertebra V3 such that tether 20 is disposed on an anterior side of transverse process TP3.

Tether 20 is threaded in a costotransverse orientation along vertebra V3 and vertebra V2. Set screw 60 of head 48 is torqued on to the portion of tether 20 disposed with screw 40 to securely fix second end 24 with vertebra V2. Tether 20 is disposed in costovertebral space CS2 on a posterior side of vertebra V2 such that tether 20 is disposed on an anterior side of transverse process TP2.

Figure 8:
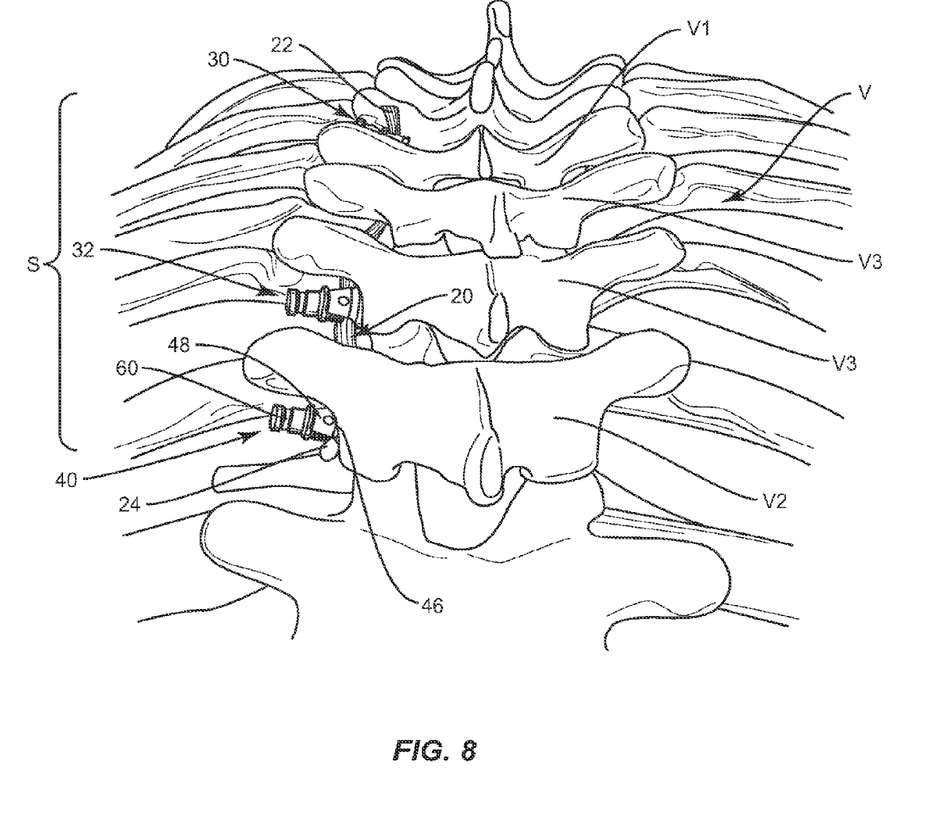
FIG. 8 is a perspective view of the components and vertebrae shown in FIG. 1.
Figure 9:
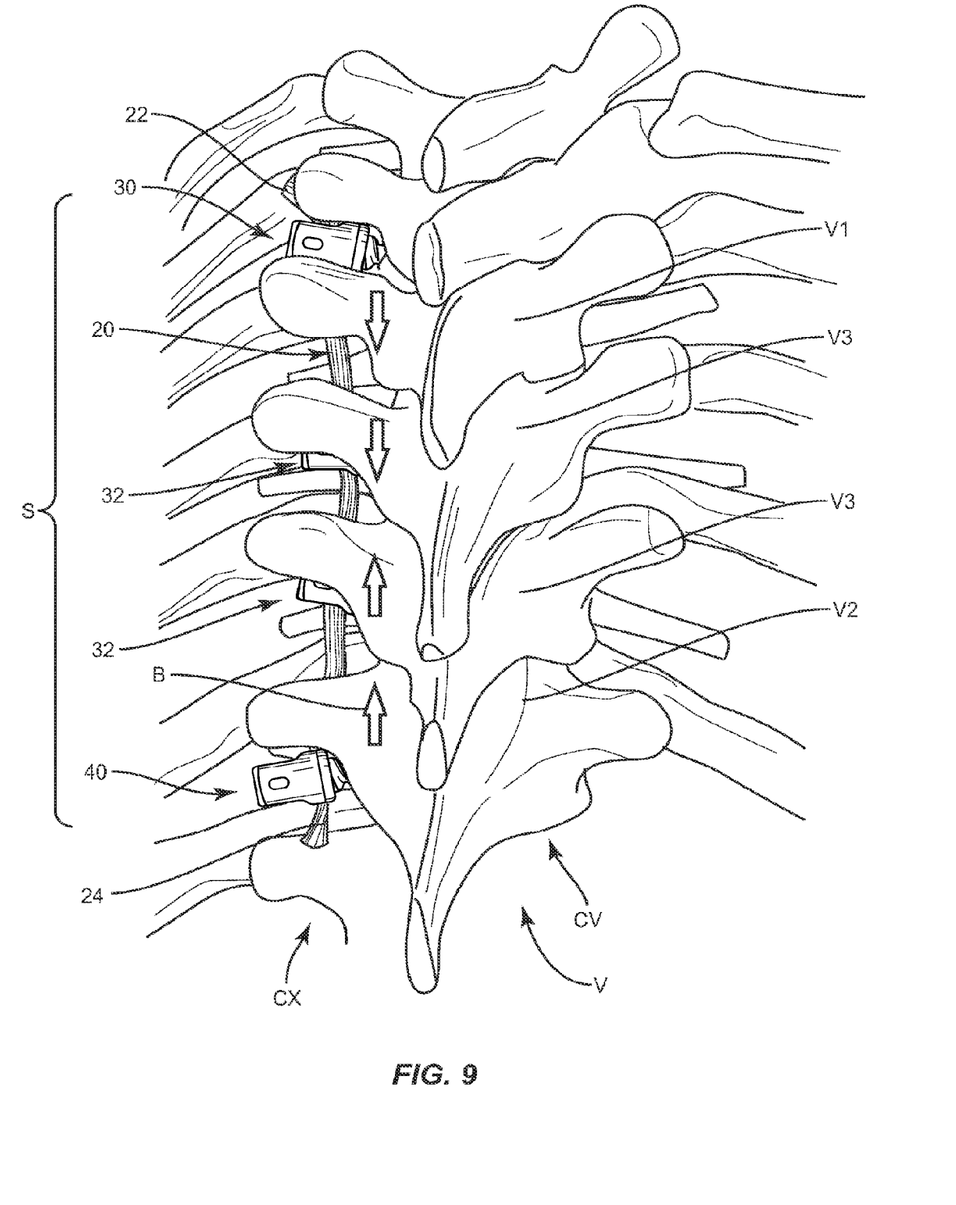
FIG. 9 is a perspective view of the components and vertebrae shown in FIG. 1.

As shown in FIGS. 1, 8 and 9, the components of the fusionless correction system are attached with a first side, such as, for example, a convex side CX of vertebrae V to prevent growth of selected section S, while allowing for growth and adjustments to a second side, such as, for example, a concave side CV of vertebrae V to provide treatment. Compression of section S of vertebrae V occurs along convex side CX, as shown by arrows B in FIG. 9. It is envisioned that this method and configuration implant components of the fusionless correction system along a sagittal plane of a patient such that tether 20 is disposed anterior to a pedicle to reduce undesired lordosis. It is further envisioned that this method and configuration implant components of the fusionless correction system along a coronal plane of a patient whereby tether 20 is disposed in a lateral orientation relative to a pedicle to provide correction in the coronal plane.

In one embodiment, the fusionless correction system includes an agent, which may be disposed, packed or layered within, on or about the components and/or surfaces of the fusionless correction system. It is envisioned that the agent may include bone growth promoting material, such as, for example, bone graft to enhance fixation of the fixation elements with vertebrae V.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of the fusionless correction system can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair spinal deterioration or damage, with the aid of the fusionless correction system. Upon completion of the procedure, the surgical instruments and assemblies are removed and the incision is closed.

In one embodiment, as shown in FIGS. 10-15, the fusionless correction system, similar to the components and method described with regard to FIGS. 1-9, includes a longitudinal element, such as, for example, a tether 120, similar to tether 20 described above, which extends between a first end 122 and a second end 124.

Figure 10:
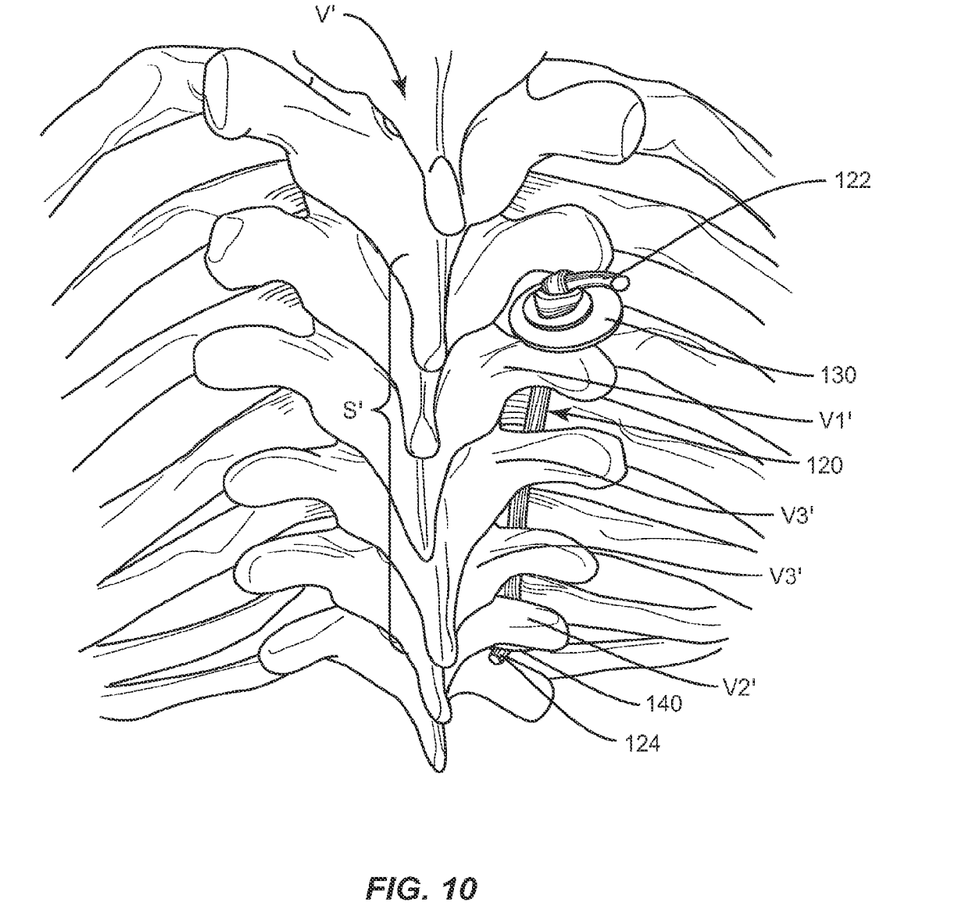
FIG. 10 a perspective view of one embodiment of a system disposed with vertebrae in accordance with the principles of the present disclosure.
Figure 11:
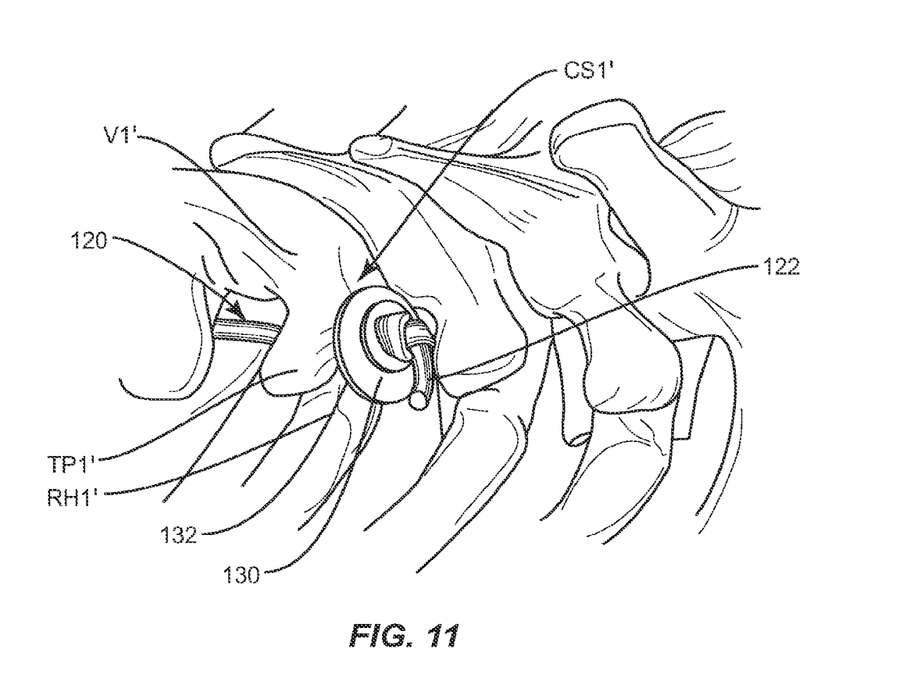
FIG. 11 is a perspective view of the components and vertebrae shown in FIG. 10.
Figure 12:
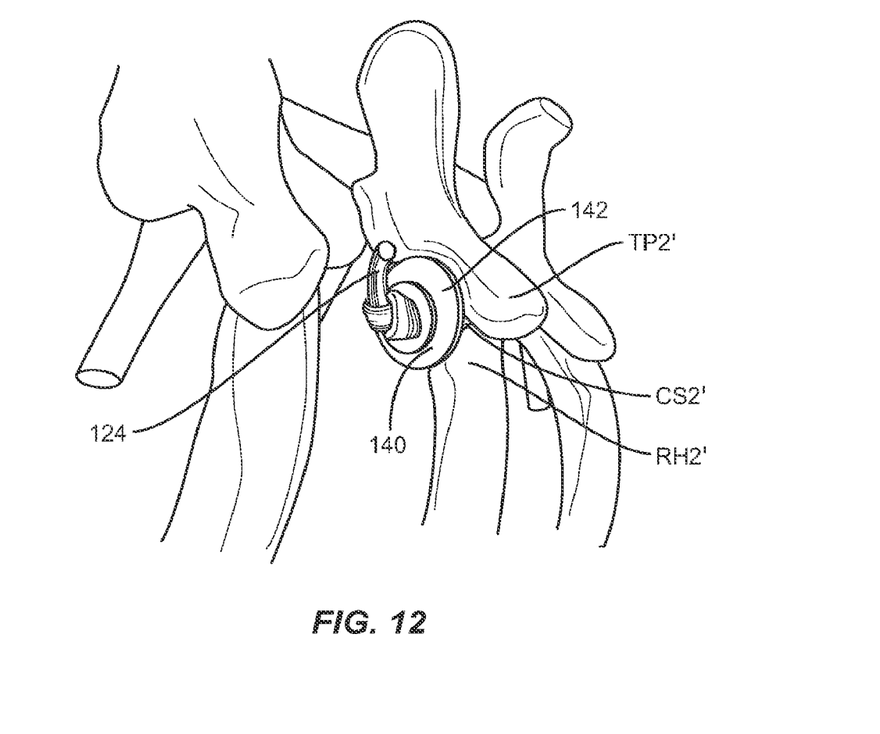
FIG. 12 is a break away perspective view of the components and vertebrae shown in FIG. 10.
Figure 13:
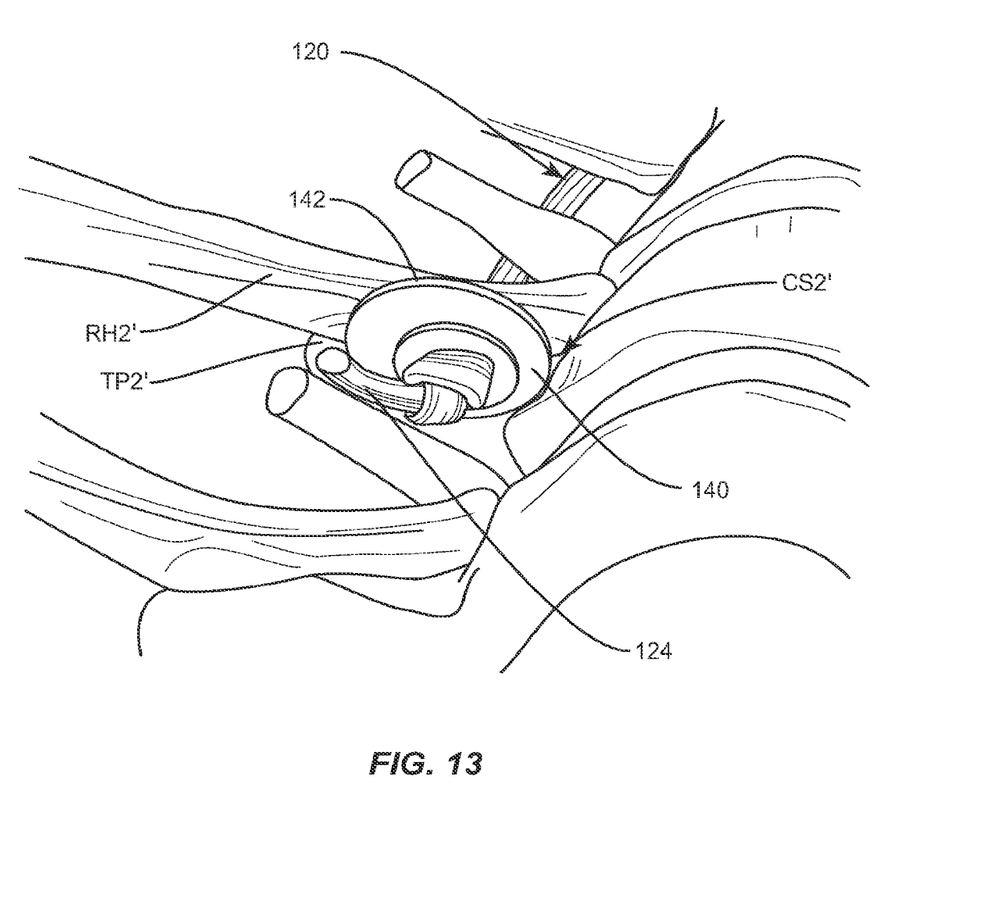
FIG. 13 is a break away perspective view of the components and vertebrae shown in FIG. 10.
Figure 14:
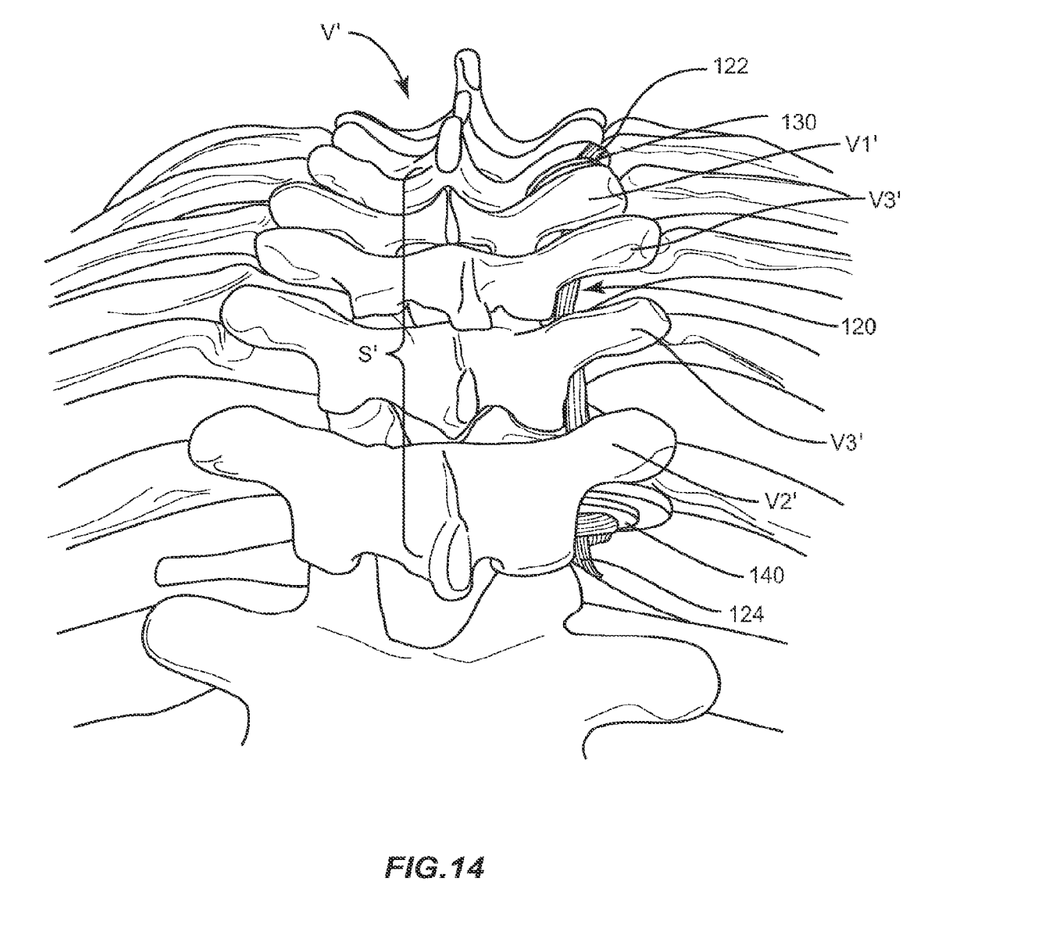
FIG. 14 is a perspective view of the components and vertebrae shown in FIG. 10.
Figure 15:
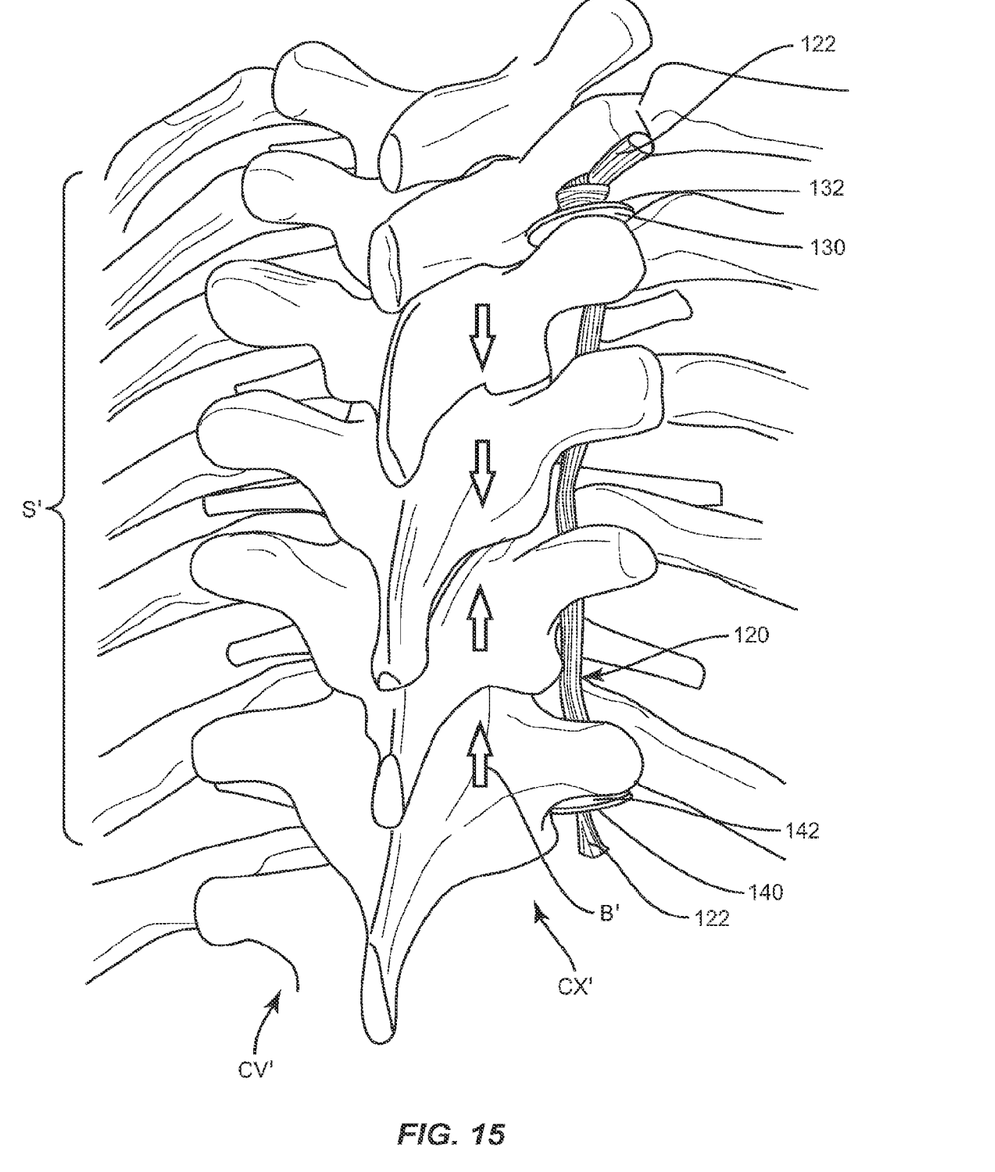
FIG. 15 is a break away perspective view of the components and vertebrae shown in FIG. 10.

A first fixation element, such as, for example, a washer 130 is connected with first end 122 and a second fixation element, such as, for example, a washer 140 is connected with second end 124. Washers 130, 140 may be monolithically formed, integrally connected or attached with fastening elements to tether 120. In one embodiment, the system may include a plurality of third fixation elements, such as, for example, washers disposed intermediate first end 122 and second end 124, and connected to tether 120 between washers 130, 140 along the length of tether 120.

Washers 130, 140 are configured for non-penetrating engagement with a costovertebral surface of a vertebra along a plurality of vertebral levels. Each of washers 130, 140 are disposed to engage a separate vertebral level. Washer 130 defines a planar surface 132 configured to engage a costovertebral surface of a vertebrae to facilitate fixation of first end 122 with the costovertebral surface. Washer 140 defines a planar surface 142 configured to engage a costovertebral surface of a vertebrae to facilitate fixation of second end 124 with the costovertebral surface. It is contemplated one or a plurality of washers may be employed with a single vertebral level. It is further contemplated that the fixation elements may be engaged with vertebrae in various orientations, such as, for example, series, parallel, offset, staggered and/or alternate vertebral levels. The washers may be coated with an osteoinductive or osteoconductive material to enhance fixation, and/or include one or a plurality of therapeutic agents. It is envisioned that ends 122, 124 may include a stop to facilitate fixation with washers 130, 140, which may include knots, endcaps, locks, clips or pins.

For example, as shown in FIGS. 10-15, the fusionless correction system including washers 130, 140 can be employed with a surgical correction treatment, similar to that described above, of an applicable condition or injury of an affected section of a spinal column and adjacent areas within a body, such as, for example, a first vertebra V1', a second vertebra V2' and a plurality of vertebra disposed therebetween, such as, for example, third vertebrae V3', of vertebrae V'.

An incision is made in the body of a patient and a cutting instrument (not shown) creates a surgical pathway along a substantially posterior approach for implantation of components of the fusionless correction system within the patient body. A sleeve or cannula is used to access a costovertebral space CS1' adjacent vertebra V1' and facilitate delivery and access for components of the fusionless correction system along the surgical pathway, for example, such that tether 120 is disposed in a costovertebral space CS1' between costovertebral surfaces, which include surfaces of a transverse process TP1', a rib head RH1' and vertebra V1'.

Washer 130 is configured to support a tensile load with tether 120 over costovertebral surfaces, which include surfaces of transverse process TP1' and rib head RH1'. With tether 120 attached to washer 130 adjacent first end 122, washer 130 is delivered along the surgical pathway adjacent costovertebral space CS1' for non-penetrating engagement with vertebra V1'. In one embodiment, tether 120 is delivered along the surgical pathway to costovertebral space CS1' for attachment with washer 130.

First end 122 of tether 120 is securely fixed to washer 130. Planar surface 132 engages the costovertebral surface of vertebra V1' such that washer 130 is fixed in a non-penetrating engagement with vertebra V1'. Tether 120 is disposed in costovertebral space CS1' on a posterior side of vertebra V1' such that tether 120 is disposed on an anterior side of transverse process TP1'. Tether 120 is threaded in a costotransverse orientation along vertebra V1' along one or a plurality of vertebral levels.

Second end 124 of tether 120 is securely fixed to washer 140. Planar surface 142 engages the costovertebral surface of vertebra V2' such that washer 140 is fixed in a non-penetrating engagement with vertebra V2'. Tether 120 is disposed in costovertebral space CS2' on a posterior side of vertebra V2' such that tether 120 is disposed on an anterior side of transverse process TP2'. In one embodiment, a plurality of washers may be utilized, disposed intermediate ends 122, 124 and vertebrae V1', V2', along a plurality of vertebral levels of vertebrae V.

The components of the fusionless correction system including washers 130, 140 are attached with a first side, such as, for example, a convex side CX' of vertebrae V' to prevent growth of selected section S', while allowing for growth and adjustments to a second side, such as, for example, a concave side CV' of vertebrae V' to provide treatment. Compression of section S' of vertebrae V' occurs along convex side CX', as shown by arrows B' in FIG. 15.

It is contemplated that the components of the fusionless correction system and method of use for fusionless tethering of deformities may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. It is further contemplated that the components of the fusionless correction system and method of use may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for fusionless correction of a spine disorder, the method comprising the steps of:
  accessing a spine;
  disposing a first end of a longitudinal element in a first aperture of a first fixation element and disposing a second end of the longitudinal element in a second aperture of a second fixation element;
  engaging a first planar surface of the first fixation element with a first costovertebral surface of a first vertebra, threading the longitudinal element in the costotransverse orientation through a plurality of costovertebral spaces disposed along a plurality of vertebral levels, and engaging a second planar surface of the second fixation element with a second costovertebral surface of a second vertebra such that the first and second planar surfaces face one another and the longitudinal element is disposed in a costotransverse orientation along a selected section of the spine; and constraining growth of the selected section of the spine with the longitudinal element.

2. A method as recited in claim 1, wherein the step of accessing the spine includes creating a pathway to a surgical site adjacent the selected section of the spine via a substantially posterior approach.

3. A method as recited in claim 1, wherein the step of accessing the spine includes a minimally invasive technique for creating a pathway to the spine.

4. A method as recited in claim 1, wherein the longitudinal element includes a tether.

5. A method as recited in claim 1, wherein the longitudinal element includes a cadaver tendon.

6. A method as recited in claim 1, wherein the longitudinal element includes a solid core.

7. A method as recited in claim 1, wherein the longitudinal element is tubular.

8. A method as recited in claim 1, wherein the first aperture extends perpendicular to the first planar surface.

9. A method as recited in claim 1, wherein:
the first fixation element includes a monolithic washer; and
the first aperture is circular.

10. A method as recited in claim 1, wherein the first end comprises a first knot having a diameter that is greater than that of the first aperture, the first knot engaging a third planar surface of the first fixation element that is opposite the first planar surface.

11. A method as recited in claim 1, wherein the longitudinal element defines an axis that extends substantially perpendicular to at least one of the first and second planar surfaces.

12. A method as recited in claim 1, wherein the step of engaging the first planar surface with the first costovertebral surface includes a non-penetrating engagement.

13. A method as recited in claim 1, wherein the step of engaging the first fixation element with the first costovertebral surface positions a portion of the longitudinal element in a costovertebral space on a posterior side of the first vertebra such that the longitudinal element is disposed on an anterior side of a transverse process of the first vertebra.

14. A method as recited in claim 13, wherein the step of engaging the second fixation element with the second costovertebral surface positions a portion of the longitudinal element in a costovertebral space on a posterior side of the second vertebra such that the longitudinal element is disposed on an anterior side of a transverse process of second first vertebra.

15. A method as recited in claim 1, wherein the first costovertebral surface is spaced apart from the second costovertebral surface over the plurality of vertebral levels.

16. A method for fusionless correction of a spine disorder, the method comprising the steps of:
accessing a surgical site adjacent a selected section of a spine along a substantially posterior approach;
disposing a first end of a flexible tether in a first aperture of a first fixation element and disposing a second end of the tether in a second aperture of a second fixation element;
threading the tether in a costotransverse orientation along a plurality of vertebral levels of the spine;
engaging a first planar surface of the first fixation element with a first costovertebral surface of a first vertebra and engaging a second planar surface of the second fixation element with a second costovertebral surface of a second vertebra such that the first and second planar surfaces face one another and the longitudinal element is disposed in a costotransverse orientation along a selected section of the spine; and
constraining growth of the selected section of the spine with the tether.

17. A method as recited in claim 16, wherein:
the first end comprises a first knot having a diameter that is greater than that of the first aperture, the first knot engaging a third planar surface of the first fixation element that is opposite the first planar surface; and
wherein the first knot is formed by interlacing a length of the tether.

18. A method for fusionless correction of a spine disorder, the method comprising the steps of:
accessing a surgical site adjacent a selected section of a spine;
threading a tether along a plurality of vertebral levels of the spine;
engaging a first planar surface of a first washer of the tether with a first costovertebral surface of a first vertebra and engaging a second planar surface of a second washer of the tether with a second costovertebral surface of a second vertebra such that the tether is disposed along the selected section of the spine, the first washer defining a first end of the tether and the second washer defining a second end of the tether; and
constraining growth of the selected section of the spine with the tether.

19. A method as recited in claim 18, wherein the tether includes a plurality of washers configured for non-penetrating engagement and being disposed intermediate the first end and the second end, and further comprising the step of engaging the plurality of washers with a plurality costovertebral surfaces disposed intermediate the first costovertebral surface and the second costovertebral surface.

* * * * *